(12) United States Patent
Dilmaghanian (10) Patent No.: US 9,466,915 B2
(45) Date of Patent: Oct. 11, 2016

(54) IN-LINE CONNECTORS AND RELATED METHODS

(71) Applicant: BAL SEAL ENGINEERING, INC., Foothill Ranch, CA (US)

(72) Inventor: Farshid Dilmaghanian, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 139 days.

(21) Appl. No.: 13/633,744

(22) Filed: Oct. 2, 2012

(65) Prior Publication Data
US 2014/0094048 A1    Apr. 3, 2014

Related U.S. Application Data

(60) Provisional application No. 61/542,379, filed on Oct. 3, 2011.

(51) Int. Cl.
*H01R 13/52* (2006.01)
*H01R 43/16* (2006.01)
*H01R 13/187* (2006.01)

(52) U.S. Cl.
CPC ........ *H01R 13/5219* (2013.01); *H01R 13/187* (2013.01); *H01R 43/16* (2013.01); *H01R 13/5224* (2013.01); *Y10T 29/49204* (2015.01)

(58) Field of Classification Search
CPC ................. H01R 13/5219; H01R 13/5224
USPC ........................................................ 439/271
See application file for complete search history.

(56) References Cited

U.S. PATENT DOCUMENTS

| 4,413,831 | A | * | 11/1983 | Washida et al. | ............... 277/386 |
| 4,655,462 | A | * | 4/1987 | Balsells | ........................ 267/167 |
| 4,826,144 | A | * | 5/1989 | Balsells | ........................ 267/167 |
| 4,876,781 | A | * | 10/1989 | Balsells | ........................ 29/896.9 |
| 4,907,788 | A | * | 3/1990 | Balsells | ........................ 267/168 |
| 7,722,415 | B2 | * | 5/2010 | Chansrivong | ................. 439/840 |
| 8,437,855 | B2 | * | 5/2013 | Sjostedt et al. | ................. 607/37 |
| 2003/0073348 | A1 | * | 4/2003 | Ries et al. | .................... 439/578 |
| 2003/0163171 | A1 | * | 8/2003 | Kast et al. | ...................... 607/36 |
| 2008/0246231 | A1 | * | 10/2008 | Sjostedt et al. | ............... 277/641 |

(Continued)

FOREIGN PATENT DOCUMENTS

WO    WO 02/16809        2/2002
WO    WO 2010/129293 A2  11/2010

OTHER PUBLICATIONS

Extended European Search Report dated Feb. 6, 2013 from corresponding European Application No. 12187067.9 (8 pages).

(Continued)

*Primary Examiner* — James Harvey
(74) *Attorney, Agent, or Firm* — Klein, O'Neill & Singh, LLP (57) ABSTRACT

An in-line connector is disclosed having a plurality of connector components attached in an in-line configuration with a common bore. Depending on the application, the in-line connector can have an end seal and a holding block for securing the in-line connector to a pin, lead, or shaft. The connector components are arranged so that at least one seal element is located between two adjacent conductive contact elements. To provided added biasing force to a seal lip of the at least one seal element, a seal groove is provided with an energizer located therein.

18 Claims, 6 Drawing Sheets

(56) References Cited

U.S. PATENT DOCUMENTS

2008/0255631 A1* 10/2008 Sjostedt et al. .................. 607/37
2010/0267265 A1* 10/2010 Dilmaghanian .............. 439/271
2010/0289198 A1* 11/2010 Balsells .................. B21F 35/00
  267/151
2011/0059639 A1* 3/2011 Dilmaghanian et al. ..... 439/271
2014/0094048 A1* 4/2014 Dilmaghanian .............. 439/271

OTHER PUBLICATIONS

Examiner's Report on corresponding foreign application (EU Application No. 12187067.9) from the European Patent Office dated Jan. 27, 2016.

* cited by examiner

IN-LINE CONNECTORS AND RELATED METHODS

FIELD OF ART

Connector assemblies having one or more conductive contact elements in spaced-apart configuration are generally discussed herein with particular discussions on connector assemblies having conductive contact element that are in a spaced apart in-line configuration for receiving a rod, shaft or a pin, with or without conductive nodes. The in-line connectors can be used for electrical transmission and/or isolation in various industries, such as in automotive, aerospace, medical, oil and gas, and consumer electronics.

BACKGROUND

Electrical contact elements can be used to connect an Implantable Pulse Generator (IPG) to the lead for Medical Electronic Devices used in Cardiac Rhythm Management (CRM) and Nuero-stimulation (pain management) applications. Exemplary contact elements are disclosed in co-pending application Ser. No. 12/100,646, entitled Integrated Header Connector System, filed Apr. 10, 2008, in Ser. No. 12/876,775, filed Sep. 7, 2010, entitled Connector Assemblies for Use with Implantable Medical Devices; and in Ser. No. 12/062,895, filed Apr. 4, 2008, entitled Connector Assemblies for Use with Implantable Medical Devices, the contents of each of which are expressly incorporated herein by reference for all purposes to the extent they do not conflict with expressly described elements and features of the presently disclosed apparatus, system, and method.

The indicated applications described in-line connectors for electrically transmitting separate signals or electrical pulses from a transmitter or transceiver housing through an-line connector to transmit signals to remotely positioned electrical pads. The multiple conductors are can transmit without electrical interference by using non-conductive seal elements to seal or isolate adjacent conductive contacts and conductive springs.

Another in-line application is disclosed in U.S. Pat. No. 7,722,415 to Changsrivong, the contents of which are expressly incorporated herein by reference for all purposes to the extent they do not conflict with expressly described elements and features of the presently disclosed apparatus, system, and method. The '415 patent is directed to connectors for connecting two elongated members that are positioned in-line to one another. Certain parts or sections of the disclosed in-line connectors in the '415 patent are collapsible to enable connection and disconnection of the two in-line elongated members in tight or confined spaces.

Other in-line applications include headphone jacks for audio and/or video devices. The multi-node jacks can transmit multiple pules or signals by isolating adjacent conductors.

SUMMARY

Aspects of the present device and system include an in-line connector comprising a seal element and a conductive contact element attached in an in-line configuration and defining a common bore, a canted coil spring in contact with the conductive contact element; and wherein the seal element comprises a seal groove comprising a cavity having an energizer located therein. The energizer can be selected to provide added biasing force on the seal element to increase sealing against a pin or a shaft that is inserted into the common bore.

The in-line connector can include a groove opening that faces away from the common bore.

The in-line connector, wherein the groove opening can partially face axially relative to the common bore or partially axially and radially outwardly, away from the common bore.

The in-line connector can further comprise an end seal comprising an opening disposed at an end of the in-line connector.

The in-line connector can further comprise a holding block comprising a bore disposed at an end of the in-line connector.

The in-line connector, wherein the seal element can comprise a second seal groove located adjacent the seal groove, said second seal groove can also have an energizer located therein like the seal groove.

The in-line connector can include a radial canted coil spring or an axial canted coil spring.

The in-line connector can further comprise two or more conductive contact elements.

The in-line connector, wherein the conductive contact element comprises a connection groove and wherein the seal element comprises a mating lip that projects into the connection groove.

Aspects of the present disclosure can further include a device with a circuit board for transmitting electrical signals. The device can comprise a housing having an in-line connector. The in-line connector can comprise a seal element and a conductive contact element attached in an in-line configuration and defining a common bore. A canted coil spring can be placed in contact with the conductive contact element and wherein the seal element can comprise a seal groove comprising a cavity having an energizer located therein.

The device as disclosed, wherein the housing can comprise a sealed implantable medical device.

The device can further comprise a pin disposed in the common bore.

The device, wherein the canted coil spring can be a radial canted coil spring or an axial canted coil spring.

The device, wherein the conductive contact element can comprise a connection groove and wherein the seal element comprises a mating lip that projects into the connection groove.

The device, wherein the seal element can comprise a second seal groove located adjacent the seal groove, said second seal groove can have an energizer located therein.

A still further aspect of the present disclosure is a seal element for use in an in-line connector. The seal element can comprise a bore defining a sealing lip, a seal body having a cavity defining a seal groove, and an energizer located in the seal groove.

The seal element, wherein the cavity comprises an opening spaced from the sealing lip.

A still further aspect of the present disclosure is a method for manufacturing an in-line connector. The method can comprise the steps of providing a conductive contact element; providing a seal element; and attaching the seal element to the conductive contact element to form a common bore. In some examples, the seal element can comprise a seal groove comprising a cavity having an energizer located therein.

The method can further comprise the step of placing a spring contact element in contact with the conductive contact element.

The method can further include the step of placing a pin, shaft, or rod into the common bore.

BRIEF DESCRIPTION OF THE DRAWINGS

These and other features and advantages of the present device, system, and method will become appreciated as the same become better understood with reference to the specification, claims and appended drawings wherein:

DETAILED DESCRIPTION

The detailed description set forth below in connection with the appended drawings is intended as a description of the presently preferred embodiments of in-line connectors provided in accordance with aspects of the present device, system, and method and is not intended to represent the only forms in which the present device, system, and method may be constructed or utilized. The description sets forth the features and the steps for constructing and using the embodiments of the present device, system, and method in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
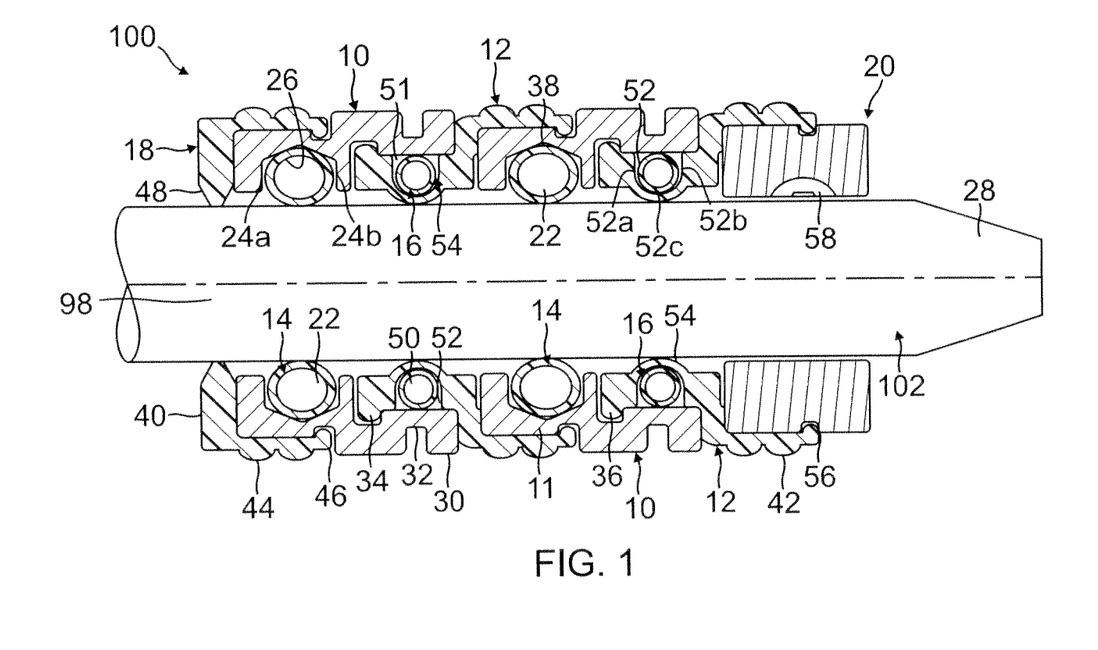
FIG. 1 is a schematic cross-sectional side view of an in-line connector provided in accordance with aspects of the present, device, system and method.

FIG. 1 is a schematic cross-sectional side view of various components that together form an in-line connector assembly 100, which may also be referred to as an in-line connector or connector assembly. In practice, the various components are annular in shape with each comprising a bore that together form a common bore. In an embodiment, the connector assembly 100 comprises one or more conductive contact elements 10 (only two shown), one or more seal elements 12 (only two shown), one or more conductive springs 14 (only two shown), and one or more energizers 16 (only two shown). The number of individual connector components, which include the conductive contact elements and conductive springs, can vary depending on the number of electrodes incorporated in a lead cable 102 for carrying separate or distinct electrical signals or currents passing through the connector assembly 100 to the electrode leads (not shown) positioned in the lead cable, which is positioned in the bore 98 of the in-line connector. The bore 98 may be referred to as a common bore as it is common to the bore of each of the various components. As an example, in a six electrode implantable medical device, at least six conductive contact elements 10 and at least six conductive springs 14 will be utilized to form the in-line connector assembly 100 for transmitting six different signals onto the lead cable having six electrode leads, as discussed in the '646 application.

In other examples, the in-line connector 100 comprises less than six conductive contact elements 10 and corresponding number of seal elements, conductive springs, and energizers, such as five conductive contact elements, four conductive contact elements, or three conductive contact elements. In still yet other examples, the in-line connector 100 comprises more than six conductive contact elements 10 and a corresponding number of seal elements, conductive springs, and energizers, such as seven conductive contact elements, ten conductive contact elements, or twenty-five conductive contact elements. In still yet another example, the lead cable 100 is simply a conductive rod, shaft, or pin having a solid core and a tapered end 28. As shown, the in-line connector 100 further comprises an end seal 18 and a holding block 20.

In one exemplary embodiment, the conductive springs are canted coil springs 14 each located within a groove 22 formed in the body 11 of the conductive contact element 10. The groove 22, which may also be referred to as a spring groove, comprises two sidewalls 24a, 24b and a bottom wall 26 located therebetween. As shown, the bottom wall is V-shape or a V-groove comprising two bottom wall sections angled relative to one another. In other embodiments, the bottom wall is a flat bottom wall orthogonal to at least one of the two sidewalls or at an angle to at least one of the two sidewalls. The groove 22 may comprise any number of geometries to permit rotation of the conductive spring 14, such as to rotate the minor axis and/or major axis of the spring, to a specified or desired position to exert a spring force against the lead cable 102, the bottom wall 26, and/or the sidewalls 24a or 24b. In other embodiments, one or both sidewalls are omitted and the adjacent seal elements expanded to form the sidewalls. As the conductive contact elements 10 are made from an electrically conductive material and the seal elements 12 are made from a non-conductive material, the spring groove having one or two sidewalls formed by or with adjacent seal elements may be referred to as a groove or spring groove made from both a conductive material and a non-conductive material. Exemplary non-limiting conductive materials useable for the present conduct contact elements include copper, bronze, aluminum, copper alloy, bronze alloy, aluminum alloy, gold or gold plated, and stainless steel. In some examples, the metallic components are coated so that they can understood to include a base metal and at least one outer coating or cladding layer. Exemplary non-limiting non-conductive seal materials include PTFE, Nitrile, Viton, Buna-N, Butyl-rubber, and various elastomers and polymers that are sufficiently elastic and compatible with the service and environment to be operated in, such as being compatible with the temperature and pressure of the environment that the in-line connector is operating. Exemplary canted coil springs are disclosed in U.S. Pat. Nos. 4,655,462; 4,826,144; 4,876,781; and 4,907,788. Canted coil springs are each understood to include a plurality of coils that are canted in the same direction and wherein each coil has a coil width, also referred to as a major axis or longer axis, and a coil height, also referred to as a minor axis or shorter axis.

A contact extension 30 extends from the body 11 of the contact element 10. In one example, the contact extension 30 comprises an axially extending ring that extends from the body in the direction of the longitudinal axis of the lead cable 102. Exteriorly, an optional first groove 32 is provided to facilitate assembly, for example to anchor the contact element 10 in a silicone header or to a non-conductive fixture (not shown) that surrounds the in-line connector 100. The groove 32, when incorporated, may instead serve as an attachment point for connecting an electrode or a conductive cable to carry current or signal from a source through to or from the conductive contact element and to or from the conductive spring 14. A second groove 38 is provided exteriorly on the body 11 for mating engagement with an adjacent seal element in a detent-like engagement. The second groove is also sometimes referred to as a body groove 38. Interiorly, a connection groove 34 is provided for mating engagement with a mating lip 36 on the seal element in a detent-like engagement. In other examples, the detent-like engagements are omitted and a friction or interference fit is utilized instead.

The electrical conductive contact elements 10 have seals located between each adjacent pair of contact elements to prevent external air, gas, or the environment external of the in-line connector from intruding or seeping into the bore 98 and the seams of the various components of the connector assembly that can affect electrical performance of the connector. The seals also prevent interference for the two adjacent conductive contact elements. In one example, the in-line connector 100 can be integrated into a header assembly and affixed to an implantable medical device (IMD). In other examples, as further discussed below, the in-line connector 100 is mounted inside a housing, such as to a music or video player, for receiving an audio or video jack. As shown, two seal element types are used with the in-line connector 100, which include the end seal 18 and the intermediate seals 12. The end seal 18 comprises an end flange 40 and an axially extending flange 42 comprising one or more projections 44 and an engagement lip or mating lip 46 for mating engagement with the body groove 38. As shown, two projections 44 are provided to function similar to an O-ring to provide compressible sealing points to seal the in-line connector 100 along its exterior surfaces, such for sealing the in-line connector inside a housing bore by pressing the projections 44 against the interior surface of the bore. At the end flange 40, an opening defined by a tapered end surface 48 is provided to seal against the rod or shaft 102. In practice, an interference fit with the shaft of about 0.5 thousandths to 1.5 thousandths is provided. In other examples, greater or less interference is used to seal against the shaft 102, which can be selected depending on the application.

The intermediate seal element 12 incorporates a groove 50, also sometimes referred to as a seal groove, which defines a cavity 51 having a groove opening 52 facing away from the lead cable 102. In one example, the groove opening 52 is covered or closed by the contact extension 30, which extends across the entire entrance of the groove opening. As shown, the opening comprises generally square edges. In other examples, one or more projections may be formed around the opening to provide added sealing against the contact extension 30. The seal groove 50 comprises two sidewalls 52a, 52b and a bottom wall 52c located therebetween. In perspective view, the groove 50 resembles a circumferential channel formed in the seal element 12. As shown, the bottom wall 52c is semi-spherical. In other examples, the bottom wall 52c is flat or angled. However, the external seal lip is preferably rounded or tapered to provide a relatively small footprint for sealing against the shaft. In other example, although less preferred, the external seal lip can have a relatively larger footprint than a tapered seal lip.

An energizer 16 is located inside the seal groove 50 to form a spring loaded seal to improve the sealing ability of the seal element 12 of the in-line connector 100. For example, by including the energizer 16, a seal may be formed against the shaft 102 at the seal projection or inward projection 54, which defines a seal lip that has a combined sealing force provided by both the elasticity of the seal material and the force supplied by the energizer for sealing against the rod or shaft. The projection 54 can have a semi-spherical shape exterior contour for pressing against the shaft. In other examples, one or more defined raised circumferential projections may be molded on the exterior surface of the projection 54 to provide a smaller surface contact with the shaft to thereby increase the contact pressure with the shaft, which is determined by the equation: Pressure=Force/Area. The energizer 16 can embody a number of types, including a helical extension spring, canted coil spring, V-spring, U-spring, O-ring, etc. As shown, an extension type spring 16 having a round cross section is used to obtain an inwardly directed force. The force is generated by stretching the inside diameter of the spring. If a canted coil spring is used inside the seal groove 106 instead, the spring force is achieved by compressing or canting the coils and/or stretching the inside diameter of the spring. If an O-ring is used, it may be stretched and placed into the seal groove 50 so that its recoiling characteristic exerts and inward force on the seal.

At an end opposite the end seal 18, a holding block 20 is provided for securing the in-line connector against the lead cable or shaft 102. In the example shown, the holding block 20 incorporates an external groove 56 for mating engagement with the mating lip 46 of the intermediate seal element 12. The holding block 20 further incorporates a set crew 58 for securing the holding block 20, and the various components by virtue of their engagements with one another, to the lead cable or shaft 102. In other examples, the holding block 20 utilizes compression fitting technology, such as that shown and described in U.S. Pat. No. 8,092,260, the contents of which are expressly incorporated herein by reference. The holding block 20 may be made from a metallic material. In other examples, the holding block 20 is made from a rigid thermoplastic material, such as from Polyvinylchloride (PVC) or Polycarbonate (PC), or from an engineered plastic, such as from Polyetheretherketone (PEEK), Polyetherketone (PEK), or Polyamides (PA).

In one example, the various connector components are axially compressed due to the various detent engagements that interconnect them. This axially compressed arrangement improves sealing ability along the various seams that separate the various connector components. The detent engagements also axially align the connector components so that the common bore 98 is more aligned than if the components are loose or easily sway and movable.

Thus, aspect of the present device, system, and method is understood to include an in-line connector comprising a plurality of alternating seal elements and conductive contact elements having a common bore, and wherein the seal elements each comprises a seal groove comprising a spring energizer located therein. In one particular embodiment, the seal grooves each comprises a groove opening that faces away from the common bore. In other embodiments, the groove opening can partially face in an axial direction relative to the common bore or face partially axially and radially outwardly away from the central bore.

Aspects of the present device, system, and method is further understood to include an axially compressed in-line connector stack comprising a plurality of connector components that include an end seal, one or more intermediate seals, one or more conductive contact elements, and at least one holding block that collectively defined a common bore for receiving a pin or a shaft; and wherein the connector components are axially compressed and the one or more intermediate seals each comprises an inward projection having an energizer disposed therein. In a further aspect of the present device, system, and method, the inward projection cam comprise a cavity having two side walls and a bottom wall having the energizer disposed therein. In particular aspects of the present device, system, and method, the inward projection comprises an opening for receiving the energizer in the cavity. The opening preferably faces away from the common bore but can be angled relative to the common bore.

In still further aspects of the present device, system, and method, a spring groove is incorporated in the conductive contact element for receiving a conductive spring, which is preferably a canted coil spring. In some embodiments, the spring groove is formed from both a conductive and a non-conductive material by incorporating at least part of one or two seal elements as sidewalls. Preferably, the spring groove is made entirely from a conductive material with both sidewalls being made from a metallic material.

Figure 2:
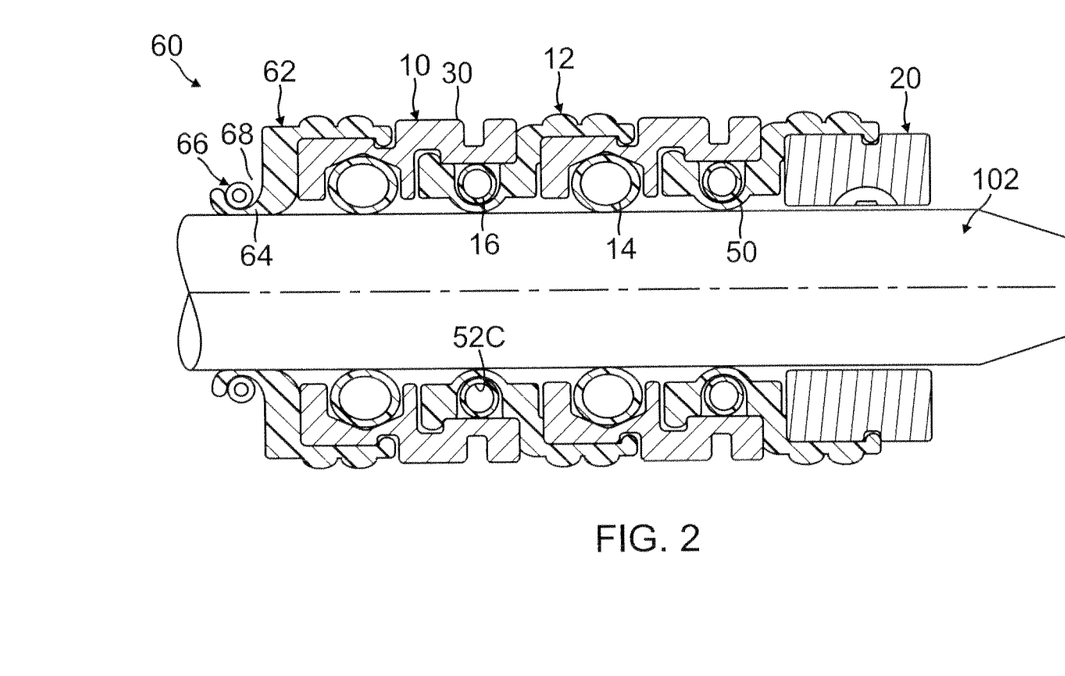
FIG. 2 is a schematic cross-sectional side view of an alternative in-line connector provided in accordance with aspects of the present, device, system and method.

FIG. 2 is a cross-sectional side view of an in-line connector assembly 60 provided in accordance with alternative aspects of the present device, system, and method. As shown, in-line connector 60 comprises a holding block 20, one or more seal elements 12, and one or more conductive contact elements 10 each with a spring contact element 14. The seal elements 12 also each includes an energizer 16 for biasing the inward projection 50 into sealing contact with the rod, shaft, pin, or lead cable 102. In the present embodiment, the end seal 62 incorporates an open sealing lip 64 for receiving an energizer 66, which can embody a helical extension spring, canted coil spring, V-spring, U-spring, or O-ring, among others. The open sealing lip 64 resembles a lip seal and has an open receiving space 68 that is not covered or obstructed.

Like the embodiment of FIG. 1, the in-line connector 60 may be used as a connection point for an IMD or for connecting to a pin or conductor for any number of electronic devices, such as an audio jack, a video jack, a connection jack that connects to an emitter, receiver, transceiver, etc.

Figure 3:
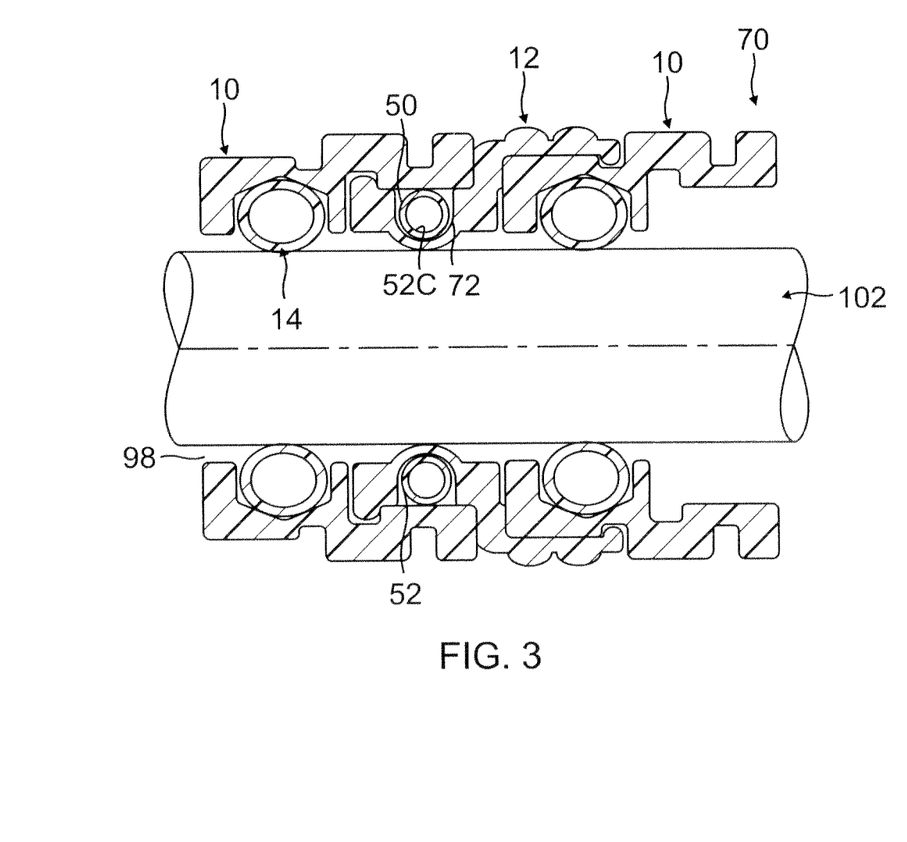
FIG. 3 is a schematic cross-sectional side view of another alternative in-line connector provided in accordance with aspects of the present, device, system and method.

FIG. 3 shows an in-line connector assembly 70 provided in accordance with alternative aspects of the present device, system, and method. The present in-line connector assembly 60 is similar to the assembly of FIG. 1 but uses a canted coil spring 72 located in the seal groove 50. The canted coil spring 72 exerts a radially inward force against the bottom wall 52c of the seal groove 52 to seal against the lead cable or shaft 102 and a radially outward force against the contact extension 30 of the conductive contact element 10, or against any other surface that is located along the outer circumference of the canted coil spring 72. For example, in another embodiment, the seal element 12 has a sealing surface located on the outer circumference of the canted coil spring 72, i.e., the channel or seal groove 52 is covered or has a non-conductive seal flap that covers the groove opening, and the spring presses outwardly against the cover (not shown).

Although not shown, the in-line connector assembly 70 is understood to include additional connector components to complete the connector assembly. For example, if the application for the connector assembly requires sealing the common bore 98, an end seal is understood to be included. If the connector 70 is to be secured to the shaft 102, a holding block is understood to be included otherwise the shaft can simply slip into the common bore and held therein by friction. Also, if the connector 70 is to be used with a single electrode or multiple electrodes, the same number of conductive contact elements and corresponding number of spring contacts are understood to be used.

Figure 4:
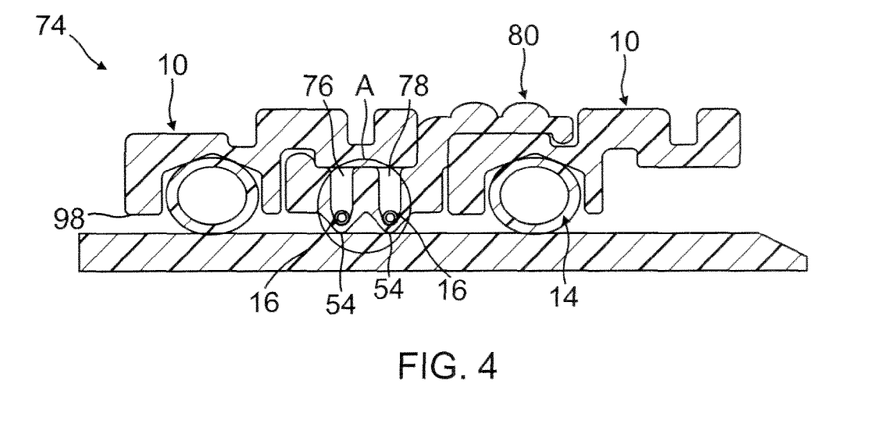
FIG. 4 is a schematic cross-sectional side view of yet another in-line connector provided in accordance with aspects of the present, device, system and method.

FIG. 4 shows an in-line connector assembly 74 provided in accordance with alternative aspects of the present device, system, and method. The present in-line connector assembly 74 is similar to the assembly of FIG. 1 but incorporates two seal grooves 76, 78 for the seal element 80 and therefore has two energizers 16 and two inward sealing projections 54. As shown, the two energizers 16 are two extension type springs. The two extension springs 16 exert inwardly directed forces on the two inward projections 54 to provide two sealing surfaces against the lead, pin, or shaft 102.

The in-line connector 74 of FIG. 4 is otherwise similar to the embodiment of FIG. 1. Thus, the in-line connector 74 is understood to include additional connector components to complete the connector assembly. For example, if the application for the connector assembly 74 requires sealing the common bore 98, an end seal is understood to be included. If the connector 74 is to be secured to the shaft 102, a holding block is understood to be included otherwise the shaft can simply slip into the common bore and held therein by friction. Also, if the connector assembly 74 is to be used with a single electrode or multiple electrodes, the same number of conductive contact elements and corresponding number of spring contacts are understood to be used.

Figure 5:
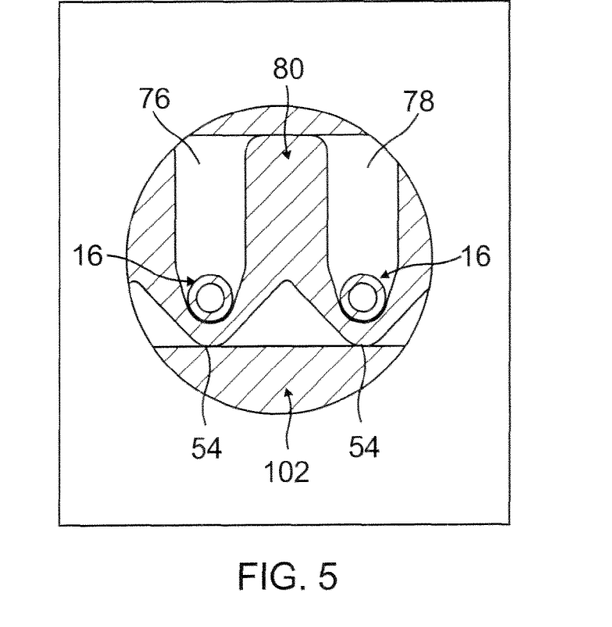
FIG. 5 is an enlarged view of point A of FIG. 4.

FIG. 5 is an enlarged view of the two seal grooves 76, 78 and two sealing lips 54 of the seal element 80, at point A, of FIG. 4.

Figure 6:
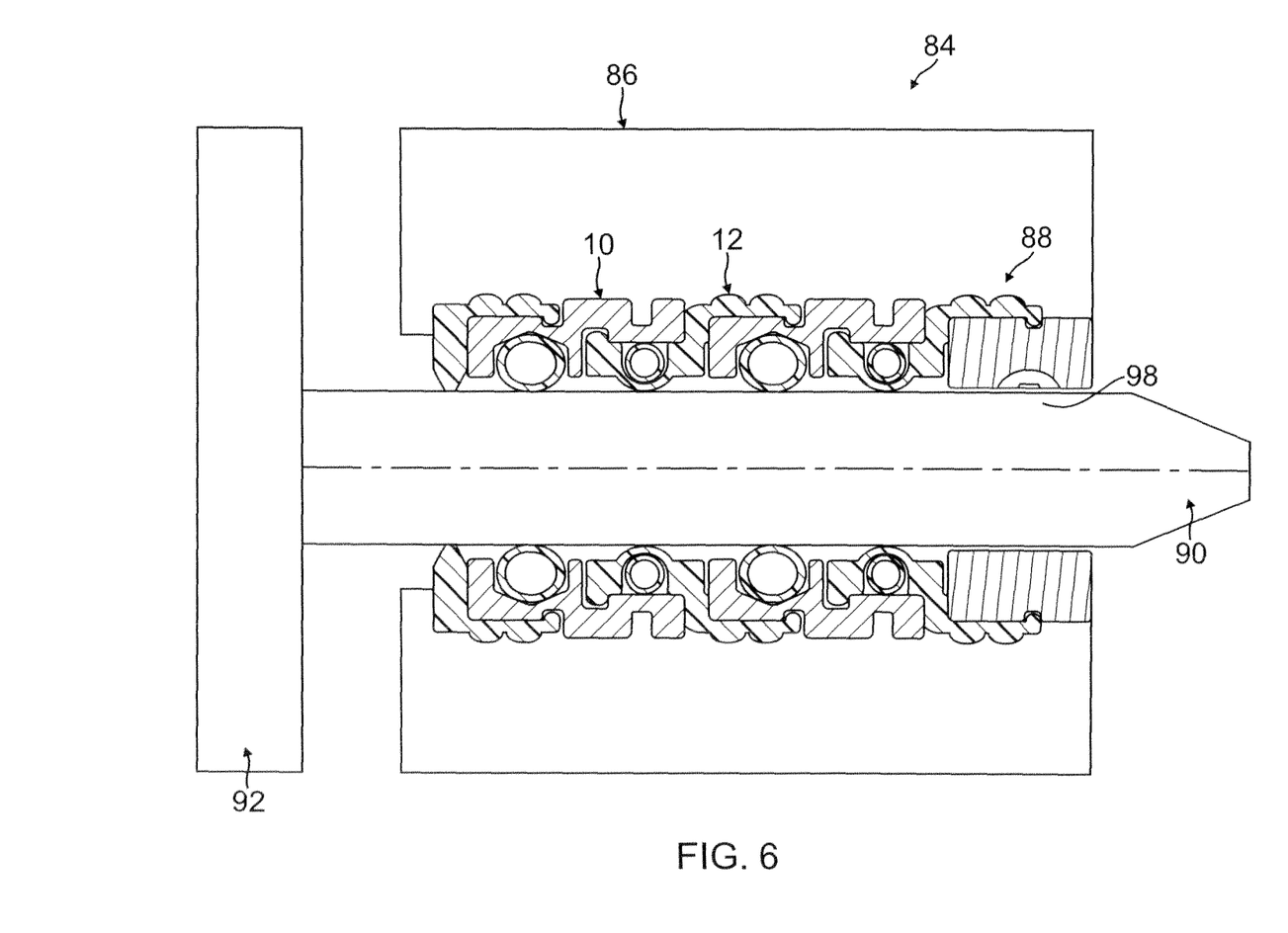
FIG. 6 is a schematic diagram depicting a system that incorporates an in-line connector of the present device, system, and method.

FIG. 6 is a schematic cross-sectional side view of a system 84 that utilizes an in-line connector assembly in accordance with aspects of the present disclosure. As shown, the system comprises a connector housing 86 comprising an in-line connector assembly 88 having a common bore 98 receiving a pin, shaft, or rod 90 connected to a pin housing 92. In practice, the connector housing 86 may comprise any number of devices or machines that utilize in-line connectors for electrical connection. For example, the housing 86 may be a sealed housing of an implantable medical device (IMD) having a header having the in-line connector assembly 88 disposed therein. The in-line connector assembly 88 can be any assemblies discussed elsewhere herein, for example the connector assembly 100 of FIG. 1. The connector housing 86 may also be a connection block in a car, on a stereo equipment, in a mainframe computer, in a game box, on an airplane, on a boat, on a train, on a satellite, at a power switching station, or at a utility substation, etc. The connection block can have electrodes or electrical leads connected to the one or more conductive contact elements 10 for transferring or receiving signals or currents to/from the pin, rod or shaft 90 via the conductive contact elements.

In one embodiment, the pin housing 92 can be any number of devices that receive or send signals to the connector housing 86 via the pin, shaft or rod 90. For example, the pin housing can be a headphone, a printed circuit board (PCB), a terminal block that branches to other electrical connections, etc.

Figure 7:
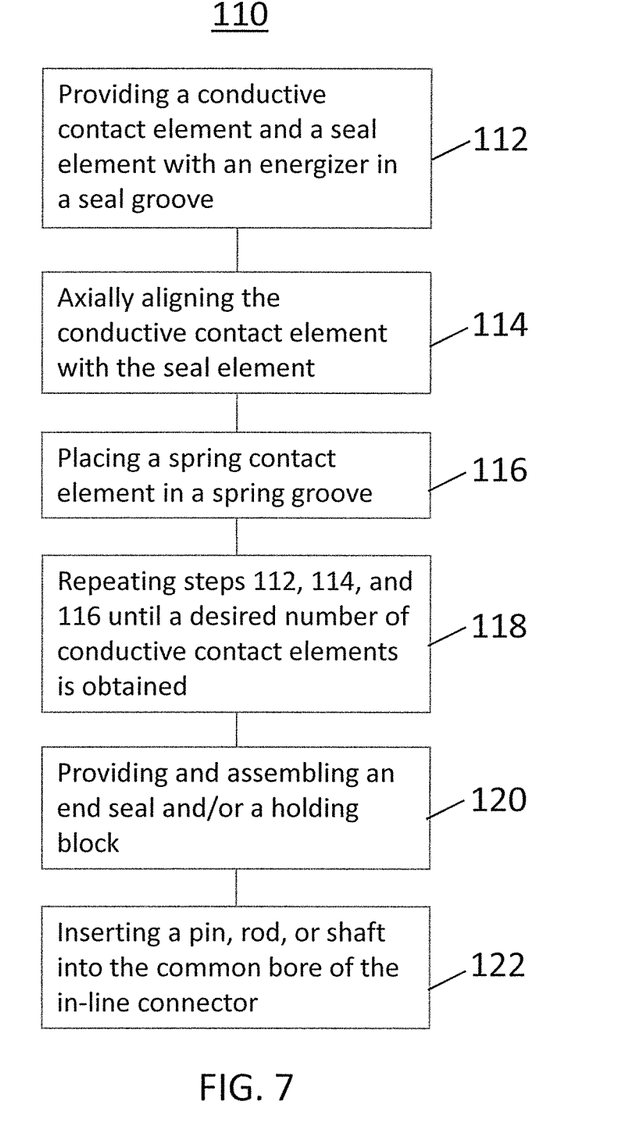
FIG. 7 is a process flow diagram depicting a method for forming an in-line connector provided in accordance with the present disclosure.

FIG. 7 is a process flow diagram depicting a process or method in accordance with aspects of the present disclosure, which is generally designated 110. In an example, the method comprises forming or providing a conductive contact element and a seal element with an energizer in a seal groove at 112. At 114, the method comprises axially aligning the conductive contact element with the seal element so that the two elements share a common bore. At 116, the method comprises placing a spring contact element in a spring groove formed at least in part by a conductive body of the conductive contact element. In some examples, the spring groove is formed with a sidewall from part of the seal element.

At 118, the method includes repeating steps 112, 114, and 116 until a desired number of conductive contact elements is obtained with each conductive contact element comprising a spring groove having a conductive spring located therein. At 120, the method comprises providing and assembling an end seal and/or a holding block if necessary or desired for the application. The method can further include the step of inserting a pin, rod, or shaft into the common bore of the in-line connector at 122.

As understood from the present disclosure, aspects of the present device, system, and method include an in-line connector comprising a conductive contact element and a seal element defining a common bore for receiving a rod or a shaft comprising a conductive electrode aligned with the conductive contact element. In an example, the conductive contact element comprises a groove having a spring contact element located therein and the seal element comprises a seal groove having an energizer located therein. In another embodiment, the seal element comprises two seal grooves having an energizer located in each of the two seal grooves. The seal grooves each comprises an opening that can be covered by an extension contact extending from a body of the contact element. In one example, the energizer located in the seal groove is an extension-type spring. In another embodiment, the energizer is a canted coil spring. In still yet another example, the energizer is an O-ring.

In accordance with a further aspect of the present disclosure, a method is provide for forming an in-line connector assembly by providing a seal groove in a seal element and placing an energizer in the seal groove. The method further comprising placing the in-line connector in a header of an implantable medical device or in a housing of an electronic device, such as a consumer electronic device.

In still another embodiment, a seal element is provided for use in an in-line connector, the seal element comprising a bore defining a sealing lip, a seal body having a cavity defining a seal groove, and a spring energizer located in the seal groove. In a specific example, the cavity comprises an opening located in a spaced apart relationship relative to the sealing lip.

Although limited embodiments of the in-line connector assemblies and their components have been specifically described and illustrated herein, many modifications and variations will be apparent to those skilled in the art. For example, the various in-line connector components may incorporate different features for engaging them to one another, different overall sizes and shapes for fitting into a particular application, etc., so long as they incorporate a seal groove having an energizer in at least one seal element located adjacent a conductive contact element comprising a spring groove. Furthermore, it is understood and contemplated that features specifically discussed for one in-line connector embodiment may be adopted for inclusion with another in-line connector embodiment provided the functions are compatible. For example, the end seal, the canted coil spring, and the energizer may be modified from, for example, a radial canted coil spring to an axial canted coil spring and from an extension spring to a V-spring or U-spring. Accordingly, it is to be understood that the in-line connector assemblies and their components constructed according to principles of the disclosed device, system, and method may be embodied other than as specifically described herein. The disclosure is also defined in the following claims.

What is claimed is:

1. An in-line connector comprising a seal element and a conductive contact element attached in an in-line configuration and defining a common bore, and a canted coil spring in contact with the conductive contact element; and wherein the seal element comprises a seal groove comprising a cavity having an energizer located therein; wherein the cavity has a groove opening that opens away from the common bore and covered by the conductive contact element, and the energizer exerts a biasing force against the seal element towards the common bore.

2. An in-line connector comprising a seal element and a conductive contact element attached in an in-line configuration and defining a common bore, and a canted coil spring in contact with the conductive contact element; and wherein the seal element comprises a seal groove comprising a cavity having an energizer located therein; wherein the cavity has a groove opening that opens away from the common bore, and the energizer exerts a biasing force against the seal element towards the common bore; wherein the energizer exerts a biasing force against the conductive contact element.

3. The in-line connector of claim 1, wherein the groove opening faces away from the common bore.

4. The in-line connector of claim 1, further comprising a pin disposed in the common bore.

5. The in-line connector of claim 1, further comprising an end seal comprising an opening disposed at an end of the in-line connector.

6. The in-line connector of claim 1, further comprising a holding block comprising a bore disposed at an end of the in-line connector.

7. The in-line connector of claim 1, wherein the seal element comprises a second seal groove located adjacent the seal groove, said second seal groove having an energizer located therein.

8. The in-line connector of claim 1, wherein the canted coil spring is a radial canted coil spring.

9. The in-line connector of claim 1, further comprising two or more conductive contact elements.

10. The in-line connector of claim 1, wherein the conductive contact element comprises a connection groove and wherein the seal element comprises a mating lip that projects into the connection groove.

11. A device with a circuit board for transmitting electrical signals comprising:
 a housing having an in-line connector, said in-line connector comprising a seal element and a conductive contact element attached in an in-line configuration and defining a common bore, and a canted coil spring in contact with the conductive contact element; and wherein the seal element comprises a seal groove comprising a cavity having an energizer located therein; wherein the cavity has a groove opening and a bottom wall opposite the groove opening, and the energizer exerts a biasing force against the bottom wall of the seal element and the conductive contact element.

12. The device of claim 11, wherein the housing comprises a sealed implantable medical device.

13. The device of claim 11, further comprising a pin disposed in the common bore.

14. The device of claim of claim 13, wherein the canted coil spring is a radial canted coil spring.

15. The device of claim 13, wherein the conductive contact element comprises a connection groove and wherein the seal element comprises a mating lip that projects into the connection groove.

16. The device of claim 11, wherein the seal element comprises a second seal groove located adjacent the seal groove, said second seal groove having an energizer located therein.

17. A method for manufacturing an in-line connector comprising:
   providing a conductive contact element;
   providing a seal element;
   attaching the seal element to the conductive contact element to form a common bore; and
   wherein the seal element comprises a seal groove comprising a cavity having an energizer located therein; wherein the cavity has a groove opening that faces away from the common bore; wherein the energizer exerts a radially inward biasing force on the seal element and a radially outward force.

18. The method of claim 17, further comprising placing a spring contact element in contact with the conductive contact element.

* * * * *